(12) United States Patent
Bian et al.

(10) Patent No.: US 10,071,150 B2
(45) Date of Patent: Sep. 11, 2018

(54) IMMUNITY ENHANCING THERAPEUTIC VACCINE FOR HPV AND RELATED DISEASES

(71) Applicant: SHENZHEN TAILAI BIOPHARMACEUTICALS, LLC, Shenzhen, Guangdong (CN)

(72) Inventors: Tao Bian, Jiangsu (CN); Juan Li, Jiangsu (CN); Xiao Xiao, Jiangsu (CN)

(73) Assignee: MYGT Biopharmaceutical LLC, Shanghai (CN)

( * ) Notice: Subject to any disclaimer, the term of this patent is extended or adjusted under 35 U.S.C. 154(b) by 0 days.

(21) Appl. No.: 15/111,758

(22) PCT Filed: Jan. 15, 2015

(86) PCT No.: PCT/CN2015/070789
§ 371 (c)(1),
(2) Date: Jul. 14, 2016

(87) PCT Pub. No.: WO2015/106697
PCT Pub. Date: Jul. 23, 2015

(65) Prior Publication Data
US 2016/0324952 A1    Nov. 10, 2016

(30) Foreign Application Priority Data
Jan. 15, 2014 (CN) .......................... 2014 1 0017909

(51) Int. Cl.
| | | |
|---|---|---|
| *A61K 39/12* | (2006.01) |
| *C07K 14/025* | (2006.01) |
| *C07K 14/35* | (2006.01) |
| *C07K 14/535* | (2006.01) |
| *C07K 14/54* | (2006.01) |
| *A61K 39/39* | (2006.01) |
| *C07K 14/005* | (2006.01) |
| *C12N 7/00* | (2006.01) |
| *A61K 39/00* | (2006.01) |

(52) U.S. Cl.
CPC .............. *A61K 39/12* (2013.01); *A61K 39/39* (2013.01); *C07K 14/005* (2013.01); *C07K 14/35* (2013.01); *C07K 14/535* (2013.01); *C12N 7/00* (2013.01); *A61K 2039/6031* (2013.01); *A61K 2039/6043* (2013.01); *C12N 2710/10343* (2013.01); *C12N 2710/20022* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | | | |
|---|---|---|---|---|
| 7,201,908 B2 * | 4/2007 | Cid-Arregui | .......... | A61K 48/00 424/204.1 |
| 8,137,674 B2 * | 3/2012 | Sung | ...................... | A61K 39/12 424/192.1 |

FOREIGN PATENT DOCUMENTS

| | | |
|---|---|---|
| CN | 1276833 A | 12/2000 |
| CN | 1679930 A | 10/2005 |
| CN | 103772508 A | 5/2014 |

OTHER PUBLICATIONS

Huang et al. DNA vaccine encoding heat shock protein 60 co-linked to HPV16 E6 and E7 tumor antigens generates more potent immunotherapeutic effects than respective E6 or E7 tumor antigens. Gynecologic Oncology 107 (2007) 404-412.*
Oosterhuis et al. Preclinical development of highly effective and safe DNA vaccines directed against HPV 16 E6 and E7. Int. J. Cancer: 129, 397-406 (2011).*
Reali et al. Comparative studies of Avipox-GM-CSF versus recombinant GM-CSF protein as immune adjuvants with different vaccine platforms. Vaccine. Apr. 22, 2005;23(22):2909-21.*
Boursnell et al. Construction and characterisation of a recombinant vaccinia virus expressing human papillomavirus proteins for immunotherapy of cervical cancer. Vaccine, 1996, 14:1485-1496.*
International Search Report issued in PCT/CN2015/0707089 dated May 13, 2015.

* cited by examiner

*Primary Examiner* — Nianxiang Zou
(74) *Attorney, Agent, or Firm* — Knobbe, Martens, Olson & Bear, LLP

(57) ABSTRACT

An immunity enhancing therapeutic vaccine includes a gene vector based on recombinant adenovirus and three elements: 1) an HPV antigen including the E6 and E7 multivalent fusion proteins of HPV types 16 and 18, 2) an immunologic adjuvant protein fused with said antigen, which protein may be a heat shock protein (HSP) of *Mycobacterium tuberculosis*, and 3) an immunostimulant, which may be granulocyte-macrophage colony stimulating factor (GM-CSF). The vaccine is used for the treatment of human papilloma virus infections and related diseases.

17 Claims, 5 Drawing Sheets
Specification includes a Sequence Listing.

IMMUNITY ENHANCING THERAPEUTIC VACCINE FOR HPV AND RELATED DISEASES

CROSS REFERENCE TO RELATED APPLICATIONS

This application is the U.S. National Phase of International Application No. PCT/CN2015/070789, filed Jan. 15, 2015, designating the U.S. and published in Chinese as WO 2015/106697 A1 on Jul. 23, 2015 which claims the benefit of Chinese Patent Application No. 201410017909.8, filed Jan. 15, 2014. Any and all applications for which a foreign or domestic priority claim is identified here or in the Application Data Sheet as filed with the present application are hereby incorporated by reference under 37 CFR 1.57.

REFERENCE TO SEQUENCE LISTING

The present application incorporates by reference the sequence listing submitted as an ASCII text filed via EFS-Web. The Sequence Listing is provided as a file entitled SEQ.txt, created on Jul. 11, 2016, which is 19.1 Kb in size.

TECHNICAL FIELD

The present invention relates to the field of vaccines, and particularly to a therapeutic vaccine for human papilloma virus (HPV) persistent infections and cervical cancer and other lesions induced thereby, more particularly to a therapeutic vaccine for HPV comprising an immune-enhancer.

BACKGROUND ART

Cervical cancer is a cancer of the second highest incidence in females worldwide, and approximately 274,000 patients die from the disease every year. All cervical cancers can be detected with HPV infections. Additionally, anal, vaginal, penile, some of oral, and laryngeal cancers are also associated with HPV infections. Although there are so far two preventive vaccines having been put on the market, they are ineffective in treating the existing HPV infections, let alone in preventing the progression of lesion malignancy. And, it is estimated that there is already a very large population of patients infected with HPV. As a result, a large scale of preventive vaccination may require at least 20 years to substantially achieve a decreased incidence of cervical cancer. In view of the large population infected with the viruses who may even have developed a cervical cancer or a precancerous lesion, there is an urgent need of the development of a therapeutic vaccine for the purpose of cleaning up those cells and cancer cells that have been infected. HPV E6 and E7 proteins are oncoproteins encoded by two oncogenes carried by HPV viruses, belong to non-autologous, exogenous protein antigens, and persist with stable expression from precancerous lesions to the occurrence of cervical cancers, and thus are ideal targets for immunotherapy. Numerous clinical studies have attempted to target these two oncoproteins, including studies on recombinant viruses, polypeptides, proteins and DNA vaccines. These therapeutic vaccines exhibit excellent safety, and show degraded lesion and prolonged survival in some of the patients. Moreover, studies indicate that the degree of T cell immunity induced by vaccination may be associated with the therapeutic effect of the treatment. However, for the purpose of completely curing persistent infections and eliminating cancers, there is still a need of a new strategy for inducing a sufficient anti-tumor T cell immune response to a specific antigen, although there is already a prospect in some of the clinical studies.

Heat shock protein (HSP) can be effective in regulating cell function and enhancing immune responses. First, it can function as a "chaperone", to assist protein transportation and positioning and protein folding; second, it can activate appropriative antigen presenting cells (APCs). HSP70 is capable of binding to a receptor on a macrophage, thereby effectively inducing an immune response thereof. SGN-00101 is a fusion protein fused with a E7 protein from HPV Type 16 and HSP65 from *Mycobacterium tuberculosis*, which has exhibited good safety and some effect on the inhibition of highly atypical proliferation in cervical epithelial cells.

Granulocyte-macrophage colony stimulating factor (GM-CSFs) has been widely studied and is recognized as one of the most effective therapeutic agents. It can mediate natural killer cells and activate CD8+ killer T lymphocytes specific to tumors through antigen presenting cells, so as to produce an anti-tumor effect. It has been demonstrated in many animal and clinical trials for the abilities to effectively stimulate tumor-suppressing immune response for a long period of time. For example, Sipuleucel-T, as an immunotherapeutic drug, is the one which takes advantage of the activation of antigen presenting cells with a GM-CSF, and now has been approved by U.S. Food and Drug Administration for marketing. The latest clinical study from Jennerex et al. also shows that oncolytic Vaccinia with an expression of a GM-CSF allows for a reduction of various cancer lesions. However, all of these immune enhancing methods have an unsatisfied therapeutic effect of either poor specificity to tumor antigen or insufficient immune stimulation.

SUMMARY

For solving the unsatisfied therapeutic effect of the prior art immune-enhancing methods of either poor specificity to tumor antigen or insufficient immune stimulation, the present invention provides a therapeutic immune-enhancing vaccine for an HPV infection and a related disease.

First, the present invention provides a fusion antigen having 5 genotypes of HPVs and an immune-enhancing factor, comprising E6 and E7 proteins from HPV Type 16, E6 and E7 proteins from HPV Type 18, and an adjuvant protein as an immune-enhancing factor.

The present invention takes a form of linear arrangement of multivalent antigens, thereby having no effect on the T cell epitopes of the fusion protein. T cell immune responses play a central role in a therapeutic vaccination. A T cell antigenic determinant can be degraded into linear short peptides in the course of antigen presentation, and a recognition site typically has only about 8 amino acids. Therefore, order variations in antigen arrangement will have no substantive effect on immune stimulation as well. In the present invention, the inventors fuse 4 antigen proteins from HPV Types 16 and 18 with a heat shock protein molecule, and the fusion of more HPV antigens can be more advantageous in allowing for providing more potential antigenic determinants, enhancing antigen presentation, increasing immune responses, and being functional for more HPV infections with different genotypes, to thereby effectively increase the population potentially benefiting from vaccine-immunization; additionally, larger proteins may be more easily degraded and presented, so as to stimulate stronger immune responses.

In one embodiment of the present invention, said fusion antigen has following one or more mutation sites including the mutation sites in E6 protein from HPV Type 16 at position 121 where glutamic acid is replaced with glycine, and position 122 where lysine is replaced with glycine; the mutation sites in E7 protein from HPV Type 16 at position 24 where cysteine is replaced with glycine, and position 26 where glutamic acid is replaced with glycine; the mutation sites in E6 protein from HPV Type 18 at position 116 where glutamic acid is replaced with glycine, and position 117 where lysine is replaced with glycine; and the mutation sites in the E7 protein from HPV Type 18 at position 27 where cysteine is replaced with glycine, and position 29 where glutamic acid is replaced with glycine.

In the present invention, point mutation of an amino acid may be performed in a region of HPV E6 protein which is to be bound to p53 protein of a cell, and in a region of E7 protein which is to be bound to pRb protein of a cell. A mutated protein will not specifically bind to either of above two proteins, so that a risk of a possibility of HPV E6 and E7 proteins to potentially transform normal cells is eliminated. It is to be noted that, in the present invention, point mutation may be conducted at only several key positions, and thus will have no effect on the antigenicity of the protein.

In the present invention, the adjuvant protein of an immune-enhancing factor may be a heat shock protein from a prokaryote or from a mammal, preferably from *Mycobacterium tuberculosis*.

In a particular embodiment of the present invention, the fusion antigen of 5 genes of HPVs and an immune-enhancing factor has an amino acid sequence represented by SEQ ID No.1.

Further, the present invention provides a recombinant gene expression vector for expressing the fusion antigen.

In one embodiment of the present invention, preferably the vector may also carry an expression cassette of an immunostimulant.

Preferably, the immunostimulant may be a granulocyte-macrophage colony-simulating factor (GM-CSF), an interleukin, an interferon or a chemokine, preferably a granulocyte-macrophage colony-simulating factor (GM-CSF).

In a particular embodiment of the present invention, the expression vector may carry a DNA fragment having a nucleotide sequence represented by SEQ ID No.3.

In the present invention, the vector may be a recombinant adenoviral vector, a recombinant adeno-associated viral vector, a recombinant retroviral vector, a recombinant lentiviral vector, a recombinant Herpes viral vector, a recombinant Vaccinia vector, or a recombinant Sandai viral vector; and may also be a non-viral vector selected from the group consisting of a naked DNA vector, a nanoparticle, a polymer or a liposome.

Further, the present invention also provides a pharmaceutical formulation for treating a disease induced by HPV infection, comprising a therapeutically effective amount of the fusion antigen as described, or a therapeutically effective amount of the recombinant gene expression vector as described.

In a preferred embodiment, the pharmaceutical formulation comprises therapeutically effective amount of the fusion antigen and an immunostimulant.

In the pharmaceutical formulation, the immunostimulant may be a granulocyte-macrophage colony-simulating factor (GM-CSF), an interleukin, an interferon, or a chemokine, preferably a granulocyte-macrophage colony-simulating factor (GM-CSF).

In a particular embodiment of the present invention, the pharmaceutical formulation aims for expressing an antigen that is a multigene fusion antigen of E6 and E7 from HPV Types 16 and 18; an adjuvant of an immune-enhancing factor that is a heat shock protein from *Mycobacterium tuberculosis* and re-fused with the aforementioned multivalent fusion protein; and an immunostimulant that is a granulocyte-macrophage colony-simulating factor (GM-CSF).

In another particular embodiment of the present invention, the pharmaceutical formulation may further comprise a pharmaceutically acceptable carrier, excipient, auxiliary, and/or the like.

In a particular embodiment of the present invention, the pharmaceutical formulation may be directly injected into a patient as a vaccine through a single injection or one or more immune-enhancing injections, to achieve the effects of immune stimulation and enhancement. Alternatively, the pharmaceutical formulation may be indirectly used as an antigen for in vitro processing and incubating autologous cells from a patient or cells from a donor, including lymphocytes, dendritic cells, tumor cells, umbilical cord blood cells, or the like, in which cells may be further injected into the patient through one or more injections, to achieve effects of immune stimulation and enhancement.

Further, the present invention provides a recombinant adenovirus, which carries the recombinant gene expression vector as described.

In a particular embodiment of the present invention, the recombinant adenovirus allows for the expression of E6 and E7 from HPV Types 16 and 18 and a granulocyte-macrophage colony-simulating factor (GM-CSF).

In another particular embodiment of the present invention, the recombinant adenovirus preferably expresses E6, E7 proteins from HPV Types 16 and 18, a heat shock protein from *Mycobacterium tuberculosis*, and a granulocyte-macrophage colony-simulating factor (GM-CSF).

In the recombinant adenovirus, the E6 and E7 proteins from HPV Types 16 and 18 may be fused with the heat shock protein from *Mycobacterium tuberculosis* to produce a multivalent fusion protein, and an expression cassette of the fusion protein may be co-expressed with an expression cassette of a GM-CSF in the same vector.

In the recombinant adenovirus, the E6 and E7 proteins from HPV Types 16 and 18 can be formed into a multivalent fusion protein, which may be not fused with the heat shock protein, and an expression cassette of the fusion protein may be co-expressed with an expression cassette of a GM-CSF in the same vector.

Further, the present invention further provides uses of the fusion antigen, the recombinant gene vector, the adenovirus, or the pharmaceutical formulation in the manufacture of medicament for the treatment of a diseases induced by HPV infection.

The diseases induced by HPV infection belongs to diseases associated with HPV chronic infection, particularly a cervical cancer a penile cancer, an anal cancer, a laryngeal cancer, an oral cancer, a head and neck cancer, a cervical precancerous lesion, and/or a cervical hyperplasia.

In vitro T lymphocyte activation experiments show that both of a vector expressing a fusion protein of HPV antigens with HSP and a vector co-expressing HPV antigens and GM-CSF can induce a stronger T cell immune response than a vector expressing singly the HPV antigens does, and a vector expressing both of the fusion protein of HPV antigens with HSP and GM-CSF can exhibit the strongest induced T cell immune response. Further, the expression of GM-CSF allows for a significant improvement of T cell immunity level in each of high and low dose groups, and an induction of more tumor-infiltrating T cells. In the tumor treatment experiments wherein the HPV antigens are expressed in mice, the evaluation results of tumor incidence and tumor size in the mice from each of the groups show that the vector with HSP fusion and the vector expressing GM-CSF allow for a better tumor clearance and recurrence inhibition, and the vector expressing both of the fusion protein of HPV antigens with HSP and the GM-CSF can exhibit the strongest effects, consistent with the results from the in vitro experiments. Thus, the present invention presents for the first time a synergistic effect of immunostimulation from a HSP fusion protein with a GM-CSF, and provides a novel method for enhancing the effect of a vaccine in treating a cervical cancer.

In accordance with the existing experimental results in mice, it is assumed that, with the same mechanism, this vaccine can also induce in human an immune response specific to the antigens expressed by HPV viruses, so as to activate and enhance a strong killing effect of specific immune cells such as T cells on HPV-infected cells and cervical cancer. In view of that such a vaccine will induce immune responses specific to two key oncoproteins of HPV viruses, i.e., E6 and E7, which are two cancer antigen proteins that are long-term expressed and capable of inducing chronic proliferation of infected cells to finally result in the development of a cancer, the vaccine can be used for treating a cervical cancer, a cervical precancerous lesion, and cervical hyperplasia induced by HPV chronic infection, and other cancers induced by HPV chronic infection such as a laryngeal cancer and an oral cancer, etc.

DETAILED DESCRIPTION OF CERTAIN EMBODIMENTS OF THE INVENTION

Following examples are provided for the purpose of illustrating the present invention, but not limiting the scope of the present invention.

Example 1. Plasmid Construction and Virus Packaging

With the genes of E6 (Genbank access number: AF373109) and E7 (AF373110) from HPV Type 18, E6 (AB818691) and E7 (KC736931) from HPV Type 16, and HSP (EU747334) from *Mycobacterium tuberculosis* as a template, codons were optimized for expression in human, and successively spliced into an open reading frame of a fusion gene with intermediate termination codon(s) removed. The complete sequence was synthesized by Genescript Corporation. In order to eliminate a risk of cell malignant transformation due to E6 and E7, point mutation was performed at some essential positions in E6 and E7 proteins from HPV 18 and 16: HPV 18 E6 protein (Glu116Gly; Lys117Gly); HPV 16 E6 protein (Glu121Gly; Lys122Gly); HPV 18 E7 protein (Cys27Gly; Glu29Gly); HPV 16 E7 protein (Cys24Gly; Glu26Gly). HPV18&16/E6/E7 has an amino acid sequence represented by SEQ ID No.1, and HPV18&16/E6/E7HSP has an amino acid sequence represented by SEQ ID No.2, and a nucleotide sequence represented by SEQ ID No.3. The cDNA of a human-derived GM-CSF gene was obtained by RT-PCR amplification (SEQ ID No.4).

Figure 1:
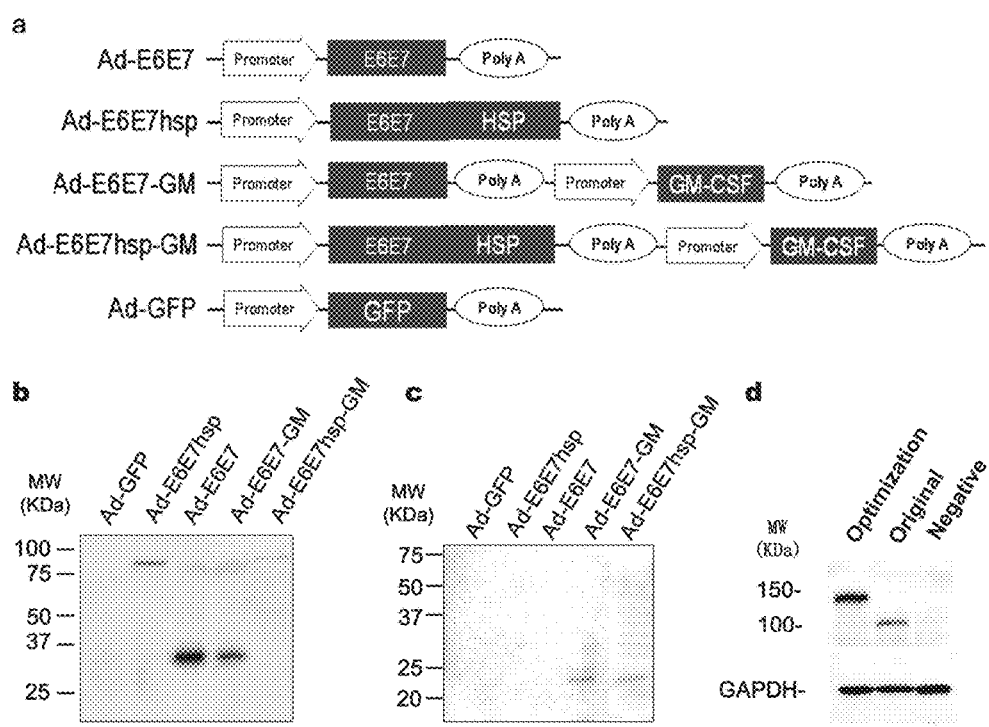
FIG. 1 is the construction and identification of a recombinant adenovirus, wherein, a shows structural patterns of 5 cDNAs of corresponding recombinant adenoviruses prepared using an Ad-easy system; b shows the expressions of the recombinant adenoviral vectors in HEK 293 cells as measured by Western blot, wherein HEK293 cells are infected with the adenoviruses, and the expression of exogenous genes are measured using an anti-HPV16E7 antibody with Ad-GFP as a negative control; c shows the expression of GM-CSF from corresponding recombinant adenovirus in HEK 293 cells as measure by Western blot; and d shows significantly increased expression of the fusion protein HPV18/16E6E7-HSP by recombinant adenovirus Ad-E6E7hsp-GM as a result of codon-optimization when compared to that without the codon optimization.

Ad-Easy adenovirus packaging system (purchased from Agilent Technologies, SantaClara, Calif.) was used to produce 5 recombinant adenoviruses. First, 5 pshuttle plasmids having different genes inserted and a CMV promoter were constructed: (1) pshuttle-E6E7, for expressing a fusion protein of HPV16 E6 and E7; (2) pshuttle-E6E7hsp, for expressing a fusion protein of HPV16 E6 and E7 with hsp; (3) pshuttle-E6E7-GM, for co-expressing human-derived GM-CSF on the basis of (1); (4) pshuttle-E6E7hsp-GM, for co-expressing the fusion protein of HPV18/16E6 and E7 with hsp and human-derived GM-CSF; and (5) pshuttle-GFP, for expressing eGFP, as a control (FIG. 1a). Then, with a conventional method, the 5 recombinant adenoviruses were packaged into Ad-E6E7, Ad-E6E7hsp, Ad-E6E7-GM, Ad-E6E7hsp-GM, and Ad-GFP, respectively.

Example 2. Measurement of Recombinant Exogenous Protein Expression

Human embryonic kidney 293 (HEK293) cells, purchased from American Type Culture Collection (ATCC, Rockville, Md.), were infected with the packaged recombinant adenoviruses prepared in Example 1 at an infection titer of 2 plaque forming units (pfu)/cell, and washed with PBS twice 2 days after the infection; then the cells were lysed with a Laemmli lysis buffer, and total cell proteins were boiled for 5 minutes for denaturation, followed by SDS electrophoresis; thereafter, the proteins were electrotransformed to a cellulose acetate membrane, and measured with corresponding antibodies: an anti-HPV16 E7 protein antibody (Santa Cruz Biotechnology, Santa Cruz, Calif.) and an anti-GM-CSF antibody (Biolegend, San Diego, Calif.). For color development, an enhanced chemiluminescence (ECL) system was used. An ELISA Assay Kit (Biolegend, San Diego, Calif.) for GM-CSF was used to measure the concentration of GM-CSF in mice.

The 5 recombinant adenoviruses were prepared in accordance with a standard method and purified by two runs of ultracentrifugation. By means of Western-Blots, the 293 cells infected with recombinant viruses were detected for the expression of the exogenous genes. As a result, it was shown that an expression band was detected at the band position of an expected molecular weight, but nothing observed at the corresponding position for a sample of a negative control with Ad-GFP infection (FIG. 1b, c). The results indicate that the fusion protein associated with the HPV antigens and GM-CSF were expressed with high efficiencies. The results of the ELISA assay show that, for the serum concentration of GM-CSF in mice, the test groups were higher than the control group by about 7 folds 5 days after injection, and still by about 1.5 folds 2 months after the injection.

The expression efficiency of HPV antigens was significantly improved after codon optimization, and the expression thereof was increased by above 3 folds than that before the optimization (FIG. 1d).

Example 3. In Vitro Lymphocyte Proliferation and ELISPOT

Female C57BL/6 mice (H-$2^b$; 6-8 weeks old) were purchased from Jackson Lab (BarHarbor, Me.), and were subcutaneously injected with viruses Ad-E6E7, Ad-E6E7hsp, Ad-E6E7-GM, Ad-E6E7hsp-GM and Ad-GFP in a dose of $10^7$ pfu/mouse. After 4 weeks, spleen cells ($1\times10^5$/well) from the mice were subjected to isolation and cultivation, and the spleen cells from each of the mice were incubated with or without 10 μg/ml of an E7 polypeptide for 5 days. BrdU was added on Day 4. The amount of BrdU fused into the cells was measured using a Calbiochem Cell Proliferation Kit (Millipore, Billerica, Mass.). The measurement results were expressed as relative increase folds which were calculated by dividing the O.D. read in the case of E7 polypeptide by the O.D. read in the case of no E7 polypeptide.

ELISPOT experiments were performed in a way of counting interferon IFNγ-secreting T lymphocytes specific to E6 and E7 polypeptides, and evaluating the immune responses from the T cells. Initially, female C57BL/6 mice were inoculated with recombinant viruses as above for immunization. After 2-4 weeks, spleen cells from the mice were subjected to isolating and cultivation in an anti-IFNγ antibody coated 96-well plate, with $1\times10^5$ cells/well. The cells from each of the mice for the culture were divided into an E6 polypeptide stimulating group and an E7 polypeptide stimulating group, and stimulated with 2 μg of an $E6_{48-57}$ (EVYDFAFRDL, H-2Db-restricted) polypeptide and an $E7_{49-57}$ (RAHYNIVTF, H-2Db-restricted) polypeptide, respectively, the cells un-stimulated with a polypeptide served as a negative control. After 24 h incubation at 37° C., cells were discarded, the residues in well were washed with 0.5% Tween 20 in PBS (PBST) for 3 times, and then were re-incubated with an anti-IFNγ antibody labeled with enzyme, and finally subjected to ACE substrate development. After the termination of the development and drying, IFNγ responsive spots were counted by an ELISPOT counter and analyzed.

Figure 2:
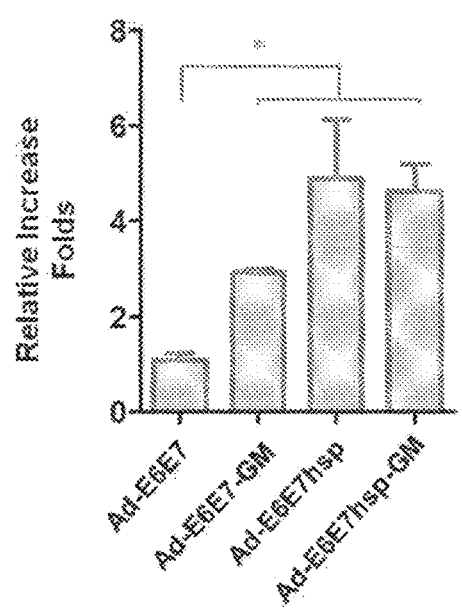
FIG. 2 shows the T lymphocytes proliferation experiment, particularly the increase folds of spleen cells in the mice immunized with corresponding recombinant adenoviruses under the stimulation with E7 polypeptide, wherein the longitudinal coordinate represents the relative increase fold, i.e., a ratio of the. O D. value of spleen cells stimulated with E7 polypeptide to the O.D. value of spleen cells unstimulated with E7 polypeptide, n=3; bars, SE; symbol "*" represents $p<0.05$.
Figure 3:
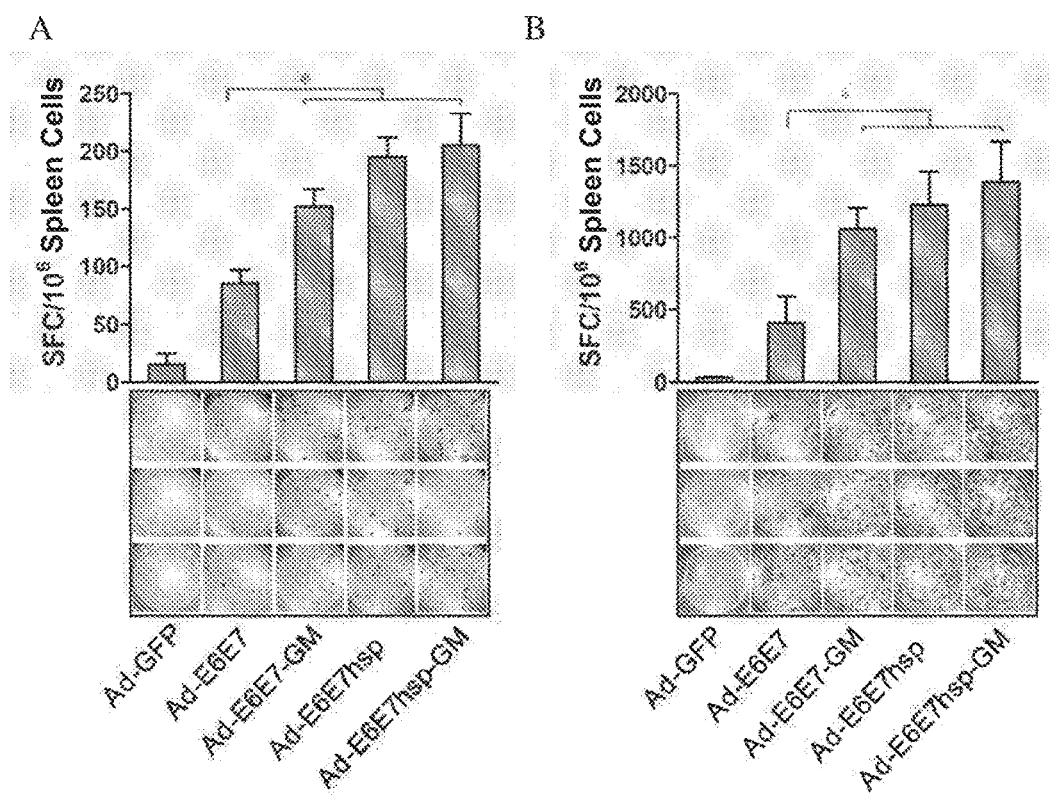
FIG. 3 shows an EISPOT experiment, wherein, A shows the amounts of IFNγ-secreting spleen cells in the mice immunized with corresponding recombinant adenovirus under the stimulation with E6 polypeptide; and B shows the amounts of IFNγ-secreting spleen cells in the mice immunized with corresponding recombinant adenovirus under the stimulation with E7 polypeptide, wherein the longitudinal coordinate represents the amount of spot forming cells per $10^6$ spleen cells, n=3; bars, SE; symbol "*" represents $p<0.05$.

Antigen-specific T cell immune response can be determined in vitro from the results of the T cell proliferation and ELISPOT experiments. In the T cell proliferation experiment, the relative cell amount on Day 5 may be expressed as the content of BrdU incorporated into cellular DNAs. Under the stimulation with the E7 specific polypeptide, all the spleen cells from the mice inoculated with the recombinant viruses expressing HPV antigens were increased much more than the spleen cells from the negative control mice immunized with Ad-GFP (FIG. 2). The murine spleen cells immunized with recombinant viruses Ad-E6E7hsp and Ad-E6E7-GM, respectively, had an increase fold higher than those inoculated with Ad-E67, and Ad-E6E7hsp-GM immunized mice showed the highest increase. The degree of the immune response from the antigen-specific killer T cells can be seen from the results of the ELISPOT experiments. The results indicate that, under the stimulation with the E6 polypeptide, all the mice immunized with the recombinant viruses expressing the HPV antigens had acquired an immune response of killer T cells specific to the antigens. Particularly, the mice immunized with each of Ad-E6E7hsp, Ad-E6E7-GM and Ad-E6E7hsp-GM had IFNγ-secreting spleen cells much more than the mice inoculated with Ad-E6E7, and the Ad-E6E7hsp-GM immunized mice had the highest amount of IFNγ-secreting spleen cells (FIG. 3A). Under the stimulation with the E7 polypeptide, IFNγ-secreting spleen cells had a relative distribution similar to that under the stimulation with the E6 polypeptide, except that the absolute amount in each of the groups was much higher than that under the stimulation with E6 polypeptide. It is indicated that E7 polypeptide also can induce an immune response of killer T cells in mice much stronger than that stimulated with E6 polypeptide (FIG. 3B). To sum up, the results of the T cell proliferation and ELISPOT experiments consistently show that HSP and GM-CSF can separately or synergistically enhance T lymphocyte immune response specific to E6, E7 antigens.

Example 4. Analysis of Tumor Infiltrating T Lymphocytes

C57BL/6 mice were inoculated with TC-1 cells (C57BL/6 mice tumor cells transformed with HPV Type 16 E6 and E7 oncoantigens is one of the most common cervical cancer model cell lines, gifted from Professor T. C. Wu, Johns Hopkins University). The C57BL/6 mice TC-1 cells were grown in a RPMI1640 complete medium containing 10% fetal bovine serum (FBS) and 50 U/ml of two antibiotics, and other cells were grown in a DMEM complete medium (Gibco). Once subcutaneous tumors were grown to a diameter of about 5 mm, the mice were inoculated subcutaneously with $1\times10^7$ of recombinant adenoviruses Ad-E6E7, Ad-E6E7hsp, Ad-E6E7-GM, Ad-E6E7hsp-GM and Ad-GFP, respectively. After 7 days, the tumors were collected and subjected to H&E dyeing and immunofluorescence analysis for anti-CD4+ and CD8+ cells, which were performed in a procedure as below: tumor tissues were removed, and subjected to freezing, OCT embedding, and cut into 5.0 μm thick sections, followed by immobilization with 4% acetone and then 30 minute blocking with 10% horse serum. Subsequently, the sections were incubated with anti-mouse CD4 and CD8 antibodies (BD Bioscience, San Jose, Calif.) at room temperature for 1 hour, and after being washed with PBS, incubated with 2 mg/mL of a goat anti-rat second antibody Alexa647 (Invitrogen, Carlsbad, Calif.). Thereafter, they were subjected to nuclear staining with DAPI and microscopic analysis. Positive cells were counted in 4 views, and designated as mean value±standard error for statistical analysis.

Figure 4:
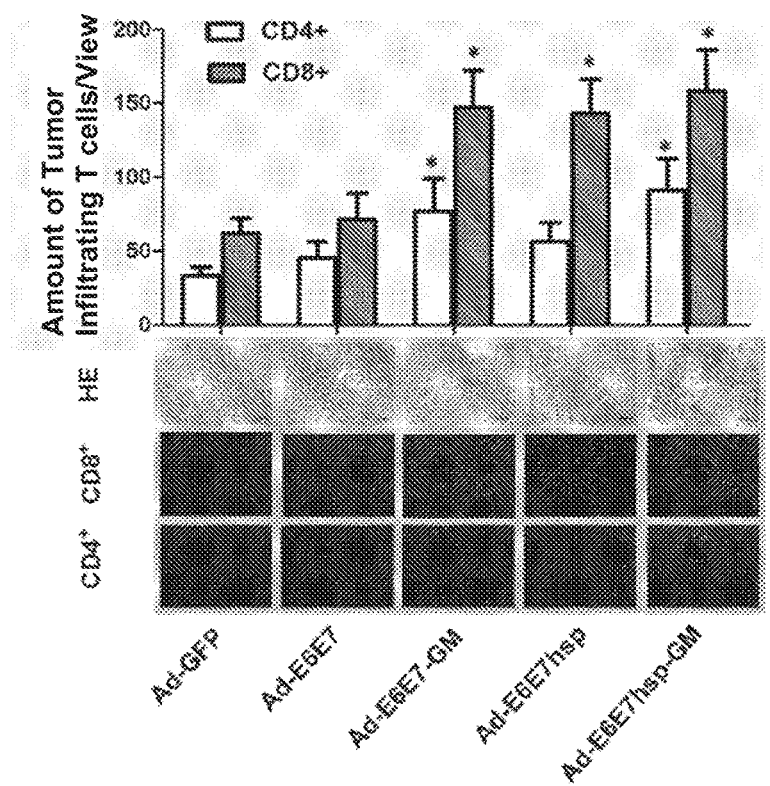
FIG. 4 shows tumor infiltrating T lymphocytes. Immunization with the recombinant adenoviruses can increase the amounts of tumor infiltrating CD8+ and CD4+ T cells. The longitudinal coordinate indicates the count of CD4+ or CD8+ T-lymphocytes in each of views, as an average of the counts of four views. bars, SE; symbol "*" represents $p<0.05$, as compared with the control Ad-GFP.

When tumor-bearing mice had tumors grown to a diameter as much as about 5 mm, the mice were subjected to immunotherapy with different recombinant adenoviruses. After 7 days, the tumors were removed for histological analysis, to evaluate the degree of T lymphocyte infiltration in the tumors from the mice immunized with the different viruses. The results of CD8+ cell staining indicate that the mice received the recombinant viruses expressing HPV antigens had more CD8+ T lymphocyte infiltration in tumor tissues than negative control mice which received immunization with Ad-GFP (FIG. 4); and both of the vectors in which a fusion protein fused with HSP and a GM-CSF were separately expressed or co-expressed were able to significantly improve the CD8+ T lymphocyte infiltration in tumor-bearing mice (FIG. 4). The results of CD4+ cell dyeing showed that, the mice which received immunization with the recombinant adenoviruses expressing GM-CSF therein had a significantly increased amount of CD4+ T lymphocyte infiltration in tumor tissues, however, the mice which received the expression of a HSP fusion protein did not have a significantly increased amount of T lymphocyte expressing CD4+ in tumor tissues, as compared to the mice immunized with Ad-E6E7 and Ad-GFP, although HSP allowed for a significant increase of CD8+ T lymphocyte infiltration (FIG. 4).

Example 5. Immunizing Dose of Recombinant Adenovirus

Three doses of $2\times10^5$, $1\times10^6$ and $1\times10^7$ pfu/mouse were used for immunizing the mice with Ad-E6E7, Ad-E6E7hsp, Ad-E6E7-GM, Ad-E6E7hsp-GM and Ad-GFP, respectively. The mice were sacrificed four weeks after the immunization, spleen cells were collected for ELISPOT experiments. IFNγ response spots of spleen cells from the mice immunized with each of various recombinant adenoviruses at each of the different doses were read and analyzed to evaluate the degrees of immunity of T cells induced by the different doses.

Figure 5:
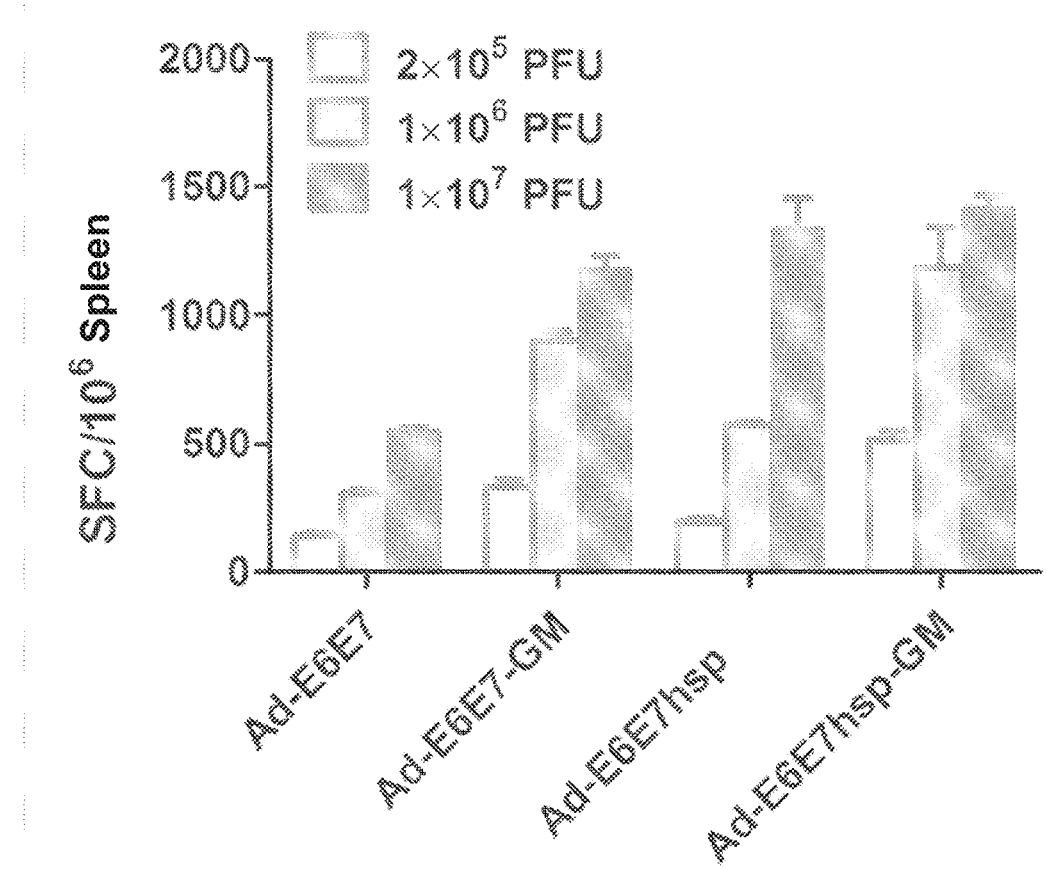
FIG. 5 shows the dose experiment of recombinant adenoviral vectors. Mice are immunized with 3 doses of corresponding recombinant adenoviruses, respectively, for ELISPOT experiment, and the amounts of IFNγ-secreting spleen cells are compared, n=3; bars, SE.

In order to evaluate the abilities of the different recombinant viruses to induce T cell immune response at different doses, the inventors conducted dose experiments. In the condition of low doses of $2\times10^5$ and $1\times10^6$ pfu/mouse, according to the amount of IFNγ-secreting cells as measured, recombinant viruses Ad-E6E7-GM and Ad-E6E7hsp-GM induced a stronger T cell immune response than the other viruses, and Ad-E6E7hsp-GM induced the strongest T cell immune response. In the condition of a high dose of $1\times10^7$ pfu/mouse, all recombinant viruses expressing HPV antigens were capable of effectively induce immune responses. Interestingly, the mice immunized with recombinant virus Ad-E6E7hsp gave rise to a larger amount of IFNγ-secreting spleen cells than that of the mice immunized with Ad-E6E7-GM, and Ad-E6E7hsp-GM immunization group still had the largest amount of IFNγ-secreting spleen cells (FIG. 5). The results indicate that GM-CSF expression can effectively enhance T cell immune response in low dose groups, while HSP fusion protein can give a better result in a high dose, and co-expression of the both enables a synergistic effect.

GM-CSF can increase the immune response of killer T lymphocytes at relatively low doses, so that a lower dose may be used to produce a better immunization result, with potential side effects reduced.

Example 6. In Vivo Tumor Treatment in Mice

This experiment is most important for evaluating therapeutic effects of the recombinant adenoviruses. First, mouse subjects were inoculated subcutaneously with $1\times10^5$/mouse of TC-1 cells; once palpable tumor masses were subcutaneously formed in the mice after about 9 days, Ad-E6E7, Ad-E6E7hsp, Ad-E6E7-GM, Ad-E6E7hsp-GM and Ad-GFP were subcutaneously injected, with doses of $1\times10^6$ and $1\times10^7$ pfu/mouse, respectively. The immunization was enhanced with the same dose 2 weeks after of initial treatment. 2 months after the initial treatment, all tumors were removed from the mice, and the mice were inoculated again with the same TC-1 cells. The mice were observed for tumor every 3 days for 4 months. Tumor incidence and tumor size were compared between the mice inoculated with different recombinant viruses, to determine the treatment and tumor clearance effects of different recombinant adenoviruses.

The results of tumor treatment experiments as above indicate that the different recombinant virus may have varied abilities of tumor cell clearance in vivo.

According to the results of the early dose tests, two doses of $1\times10^6$ and $1\times10^7$ pfu/mouse were used for the treatment experiments. In the case of a dose of $1\times10^6$ pfu/mouse, all 5 mice of the control group treated with Ad-GFP developed tumors. Only 2 of 10 mice treated with Ad-E6E7, 6 of 10 mice treated with Ad-E6E7hsp, 5 of 10 mice treated with Ad-E6E7-GM, and 7 of 10 mice treated with Ad-E6E7hsp-GM, were devoid of tumor bearing 2 months after the treatment. The results show that the latter had the best therapeutic effect. In addition, in the case of a dose of $1\times10^7$ pfu/mouse, after 2 months, all 5 mice of the control group treated with Ad-GFP developed tumors, but 4 of 5 mice treated with Ad-E6E7 were devoid of tumor bearing, and all the mice treated with Ad-E6E7hsp, Ad-E6E7-GM and Ad-E6E7hsp-GM bore no tumor (Table 1). In addition, over the same period of time, the tumor-bearing mice treated with Ad-E6E7hsp had a tumor size less than that of the mice treated with Ad-E6E7 (not shown). 2 months after the initial treatment, all mice with no tumor bearing were re-inoculated with TC-1 tumor cells. Until the end of the six-month experiment, all of the mice which were re-incubated with a tumor were still devoid of tumor bearing. In summary, the results show that HSP and GM-CSF can function separately or synergistically to achieve the effect of enhancing HPV-specific T cell immune response, and in turns clearing up tumors in mice and preventing reoccurrence. The results indicate that a combination of HSP with GM-CSF enables the best synergistical therapeutic effect.

TABLE 1

Percentages of the mice with no tumor-bearing in the tumor treatment experiments

| | | $1 \times 10^6$ | | | $1 \times 10^7$ | |
|---|---|---|---|---|---|---|
| | Mouse numbers | Mouse numbers with no tumor-bearing | Percent ages | Mouse numbers | Mouse numbers with no tumor-bearing | Percent ages |
| Ad-GFP | 5 | 0 | 0 | 5 | 0 | 0 |
| Ad-E6E7 | 10 | 2 | 20% | 5 | 4 | 80% |
| Ad-E6E7-GM | 10 | 5 | 50% | 5 | 5 | 100% |
| Ad-E6E7hsp | 10 | 6 | 60% | 5 | 5 | 100% |
| Ad-E6E7hsp-GM | 10 | 7 | 70% | 5 | 5 | 100% |

Above described are merely preferred embodiments of the present invention. It should be noted that, for the ordinary skilled in the art, some modifications and variations may be made without departing from the principles of the present invention, which modifications and variations should be deemed as being within the protection of the present invention.

INDUSTRIAL APPLICABILITY

The inventive vaccines are effective in enhancing immune responses and eliminating tumors, and are useful for treating cervical cancer, cervical precancerous lesions, cervical hyperplasia and other cancers such as some of laryngeal, oral and anal cancers, etc. induced by HPV chronic infection.

What is claimed is:

1. A fusion antigen comprising
   an E6 protein from human papilloma virus (HPV) Type 16;
   an E7 protein from HPV Type 16;
   an E6 protein from HPV Type 18;
   an E7 protein from HPV Type 18, and
   an immunologic adjuvant protein,
   wherein the fusion antigen further comprises one or more mutations positioned in a p53-interaction region of an E6 protein and/or a pRb interaction region of an E7 protein, and wherein the one or more mutations is selected from the group consisting of E121G mutation in the E6 protein from HPV Type 16, K122G mutation in the E6 protein from HPV Type 16, E116G mutation in the E6 protein from HPV Type 18, and K117G mutation in the E6 protein from HPV Type 18.

2. The fusion antigen according to claim 1, wherein the immunologic adjuvant protein is a heat shock protein from a prokaryote or a mammal.

3. A recombinant gene expression vector for expressing the fusion antigen according to claim 1.

4. The recombinant gene expression vector according to claim 3, wherein the recombinant gene expression vector carries an expression cassette for expressing the fusion antigen according to claim 1, and an expression cassette for expressing an immunostimulant.

5. The recombinant gene expression vector according to claim 4, wherein the immunostimulant is a granulocyte-macrophage colony-stimulating factor (GM-CSF), an interleukin, an interferon, or a chemokine.

6. The recombinant gene expression vector according to claim 3, wherein the recombinant gene expression vector carries a DNA fragment having the nucleotide sequence represented by SEQ ID NO: 3.

7. The recombinant gene expression vector according to claim 3, wherein the recombinant gene expression vector is a recombinant adenoviral vector, a recombinant adeno-associated viral vector, a recombinant retroviral vector, a recombinant lentiviral vector, a recombinant Herpes viral vector, a recombinant Vaccinia vector, or a recombinant Sandai viral vector.

8. The recombinant gene expression vector according to claim 3, wherein the recombinant gene expression vector comprises a non-viral vector selected from the group consisting of a naked DNA vector, a nanoparticle, a polymer, and a liposome.

9. A pharmaceutical formulation for treating a disease induced by an HPV infection, comprising a therapeutically effective amount of the fusion antigen according to claim 1, or a therapeutically effective amount of the recombinant gene expression vector for expressing the fusion antigen.

10. The pharmaceutical formulation according to claim 9, wherein the pharmaceutical formulation comprises a therapeutically effective amount of the fusion antigen, and an immunostimulant.

11. The pharmaceutical formulation according to claim 10, wherein the immunostimulant is a granulocyte-macrophage colony-stimulating factor (GM-CSF), an interleukin, an interferon, or a chemokine.

12. A recombinant adenovirus comprising the recombinant gene expression vector according to claim 3.

13. A method of manufacturing a medicament for the treatment of a disease induced by an HPV infection, the method comprising:
    formulating the medicament with the fusion antigen according to claim 1, a recombinant gene expression vector for expressing the fusion antigen, or a recombinant adenovirus comprising the recombinant gene expression vector, and a pharmaceutically acceptable carrier.

14. A method of treating a disease induced by an HPV infection, the method comprising:
    administering a therapeutically effective amount of the medicament of claim 13 to a subject in need of such treatment, wherein the disease induced by the HPV infection belongs to a disease associated with an HPV chronic infection.

15. The method according to claim 14, wherein the disease induced by the HPV infection is selected from the group consisting of a cervical cancer, a penile cancer, an anal cancer, a laryngeal cancer, an oral cancer, a head and neck cancer, a cervical precancerous lesion, and cervical hyperplasia.

16. The fusion antigen according to claim 1, wherein the immunologic adjuvant protein comprises a heat shock protein from *Mycobacterium tuberculosis*.

17. The fusion antigen according to claim 1, further comprising one or more additional mutations selected from the group consisting of C24G mutation in the E7 protein from HPV Type 16, E26G mutation in the E7 protein from HPV Type 16, C27G mutation in the E7 protein from HPV Type 18, and E29G mutation in the E7 protein from HPV Type 18.

* * * * *

SEQUENCE LISTING

```
<160> NUMBER OF SEQ ID NOS: 4

<210> SEQ ID NO 1
<211> LENGTH: 520
<212> TYPE: PRT
<213> ORGANISM: Artificial Sequence
<220> FEATURE:
<223> OTHER INFORMATION: HPV18 E6/HPV18 E7/HPV16 E6/HPV16 E7 fusion
      protein

<400> SEQUENCE: 1

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Gly Gly Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val Met His
145                 150                 155                 160

Gly Pro Lys Ala Thr Leu Gln Asp Ile Val Leu His Leu Glu Pro Gln
                165                 170                 175

Asn Glu Ile Pro Val Asp Leu Leu Gly His Gly Gln Leu Ser Asp Ser
            180                 185                 190

Glu Glu Glu Asn Asp Glu Ile Asp Gly Val Asn His Gln His Leu Pro
        195                 200                 205
```

Ala Arg Arg Ala Glu Pro Gln Arg His Thr Met Leu Cys Met Cys Cys
             210                 215                 220

Lys Cys Glu Ala Arg Ile Glu Leu Val Val Glu Ser Ser Ala Asp Asp
225                 230                 235                 240

Leu Arg Ala Phe Gln Gln Leu Phe Leu Asn Thr Leu Ser Phe Val Cys
                245                 250                 255

Pro Trp Cys Ala Ser Gln Gln Ser Met His Gln Lys Arg Thr Ala Met
            260                 265                 270

Phe Gln Asp Pro Gln Glu Arg Pro Arg Lys Leu Pro Gln Leu Cys Thr
        275                 280                 285

Glu Leu Gln Thr Thr Ile His Asp Ile Ile Leu Glu Cys Val Tyr Cys
    290                 295                 300

Lys Gln Gln Leu Leu Arg Arg Glu Val Tyr Asp Phe Ala Phe Arg Asp
305                 310                 315                 320

Leu Cys Ile Val Tyr Arg Asp Gly Asn Pro Tyr Ala Val Cys Asp Lys
                325                 330                 335

Cys Leu Lys Phe Tyr Ser Lys Ile Ser Glu Tyr Arg His Tyr Cys Tyr
            340                 345                 350

Ser Leu Tyr Gly Thr Thr Leu Glu Gln Gln Tyr Asn Lys Pro Leu Cys
        355                 360                 365

Asp Leu Leu Ile Arg Cys Ile Asn Cys Gln Lys Pro Leu Cys Pro Glu
    370                 375                 380

Gly Gly Gln Arg His Leu Asp Lys Lys Gln Arg Phe His Asn Ile Arg
385                 390                 395                 400

Gly Arg Trp Thr Gly Arg Cys Met Ser Cys Cys Arg Ser Ser Arg Thr
                405                 410                 415

Arg Arg Glu Thr Gln Leu Met His Gly Asp Thr Pro Thr Leu His Glu
            420                 425                 430

Tyr Met Leu Asp Leu Gln Pro Glu Thr Thr Asp Leu Tyr Gly Tyr Gly
        435                 440                 445

Gln Leu Asn Asp Ser Ser Glu Glu Glu Asp Glu Ile Asp Gly Pro Ala
    450                 455                 460

Gly Gln Ala Glu Pro Asp Arg Ala His Tyr Asn Ile Val Thr Phe Cys
465                 470                 475                 480

Cys Lys Cys Asp Ser Thr Leu Arg Leu Cys Val Gln Ser Thr His Val
                485                 490                 495

Asp Ile Arg Thr Leu Glu Asp Leu Leu Met Gly Thr Leu Gly Ile Val
            500                 505                 510

Cys Pro Ile Cys Ser Gln Lys Pro
        515                 520

<210> SEQ ID NO 2
<211> LENGTH: 1145
<212> TYPE: PRT
<213> ORGANISM: Artificial Sequence
<220> FEATURE:
<223> OTHER INFORMATION: HPV18 E6/HPV18 E7/HPV16 E6/HPV16 E7/HSP70
      fusion protein

<400> SEQUENCE: 2

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala

```
                35                  40                  45
        Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
        65                  70                  75                  80

Tyr Ser Asp Ser Val Tyr Gly Asp Thr Leu Glu Lys Leu Thr Asn Thr
                            85                  90                  95

Gly Leu Tyr Asn Leu Leu Ile Arg Cys Leu Arg Cys Gln Lys Pro Leu
                        100                 105                 110

Asn Pro Ala Gly Gly Leu Arg His Leu Asn Glu Lys Arg Arg Phe His
                    115                 120                 125

Asn Ile Ala Gly His Tyr Arg Gly Gln Cys His Ser Cys Cys Asn Arg
                130                 135                 140

Ala Arg Gln Glu Arg Leu Gln Arg Arg Glu Thr Gln Val Met His
        145                 150                 155                 160

Gly Pro Lys Ala Thr Leu Gln Asp Ile Val Leu His Leu Glu Pro Gln
                        165                 170                 175

Asn Glu Ile Pro Val Asp Leu Leu Gly His Gly Gln Leu Ser Asp Ser
                    180                 185                 190

Glu Glu Glu Asn Asp Glu Ile Asp Gly Val Asn His Gln His Leu Pro
                195                 200                 205

Ala Arg Arg Ala Glu Pro Gln Arg His Thr Met Leu Cys Met Cys Cys
        210                 215                 220

Lys Cys Glu Ala Arg Ile Glu Leu Val Val Glu Ser Ser Ala Asp Asp
        225                 230                 235                 240

Leu Arg Ala Phe Gln Gln Leu Phe Leu Asn Thr Leu Ser Phe Val Cys
                        245                 250                 255

Pro Trp Cys Ala Ser Gln Gln Ser Met His Gln Lys Arg Thr Ala Met
                    260                 265                 270

Phe Gln Asp Pro Gln Glu Arg Pro Arg Lys Leu Pro Gln Leu Cys Thr
                275                 280                 285

Glu Leu Gln Thr Thr Ile His Asp Ile Ile Leu Glu Cys Val Tyr Cys
        290                 295                 300

Lys Gln Gln Leu Leu Arg Arg Glu Val Tyr Asp Phe Ala Phe Arg Asp
        305                 310                 315                 320

Leu Cys Ile Val Tyr Arg Asp Gly Asn Pro Tyr Ala Val Cys Asp Lys
                        325                 330                 335

Cys Leu Lys Phe Tyr Ser Lys Ile Ser Glu Tyr Arg His Tyr Cys Tyr
                    340                 345                 350

Ser Leu Tyr Gly Thr Thr Leu Glu Gln Gln Tyr Asn Lys Pro Leu Cys
                355                 360                 365

Asp Leu Leu Ile Arg Cys Ile Asn Cys Gln Lys Pro Leu Cys Pro Glu
        370                 375                 380

Gly Gly Gln Arg His Leu Asp Lys Lys Gln Arg Phe His Asn Ile Arg
        385                 390                 395                 400

Gly Arg Trp Thr Gly Arg Cys Met Ser Cys Cys Arg Ser Ser Arg Thr
                        405                 410                 415

Arg Arg Glu Thr Gln Leu Met His Gly Asp Thr Pro Thr Leu His Glu
                    420                 425                 430

Tyr Met Leu Asp Leu Gln Pro Glu Thr Thr Asp Leu Tyr Gly Tyr Gly
                435                 440                 445

Gln Leu Asn Asp Ser Ser Glu Glu Glu Asp Glu Ile Asp Gly Pro Ala
        450                 455                 460
```

```
Gly Gln Ala Glu Pro Asp Arg Ala His Tyr Asn Ile Val Thr Phe Cys
465                 470                 475                 480

Cys Lys Cys Asp Ser Thr Leu Arg Leu Cys Val Gln Ser Thr His Val
                485                 490                 495

Asp Ile Arg Thr Leu Glu Asp Leu Leu Met Gly Thr Leu Gly Ile Val
            500                 505                 510

Cys Pro Ile Cys Ser Gln Lys Pro Met Ala Arg Ala Val Gly Ile Asp
            515                 520                 525

Leu Gly Thr Thr Asn Ser Val Val Ser Val Leu Glu Gly Gly Asp Pro
        530                 535                 540

Val Val Val Ala Asn Ser Glu Gly Ser Arg Thr Thr Pro Ser Ile Val
545                 550                 555                 560

Ala Phe Ala Arg Asn Gly Glu Val Leu Val Gly Gln Pro Ala Lys Asn
                565                 570                 575

Gln Ala Val Thr Asn Val Asp Arg Thr Val Arg Ser Val Lys Arg His
            580                 585                 590

Met Gly Ser Asp Trp Ser Ile Glu Ile Asp Gly Lys Lys Tyr Thr Ala
        595                 600                 605

Pro Glu Ile Ser Ala Arg Ile Leu Met Lys Leu Lys Arg Asp Ala Glu
610                 615                 620

Ala Tyr Leu Gly Glu Asp Ile Thr Asp Ala Val Ile Thr Thr Pro Ala
625                 630                 635                 640

Tyr Phe Asn Asp Ala Gln Arg Gln Ala Thr Lys Asp Ala Gly Gln Ile
                645                 650                 655

Ala Gly Leu Asn Val Leu Arg Ile Val Asn Glu Pro Thr Ala Ala Ala
            660                 665                 670

Leu Ala Tyr Gly Leu Asp Lys Gly Glu Lys Glu Gln Arg Ile Leu Val
        675                 680                 685

Phe Asp Leu Gly Gly Gly Thr Phe Asp Val Ser Leu Leu Glu Ile Gly
    690                 695                 700

Glu Gly Val Val Glu Val Arg Ala Thr Ser Gly Asp Asn His Leu Gly
705                 710                 715                 720

Gly Asp Asp Trp Asp Gln Arg Val Val Asp Trp Leu Val Asp Lys Phe
                725                 730                 735

Lys Gly Thr Ser Gly Ile Asp Leu Thr Lys Asp Lys Met Ala Met Gln
            740                 745                 750

Arg Leu Arg Glu Ala Ala Glu Lys Ala Lys Ile Glu Leu Ser Ser Ser
        755                 760                 765

Gln Ser Thr Ser Ile Asn Leu Pro Tyr Ile Thr Val Asp Ala Asp Lys
    770                 775                 780

Asn Pro Leu Phe Leu Asp Glu Gln Leu Thr Arg Ala Glu Phe Gln Arg
785                 790                 795                 800

Ile Thr Gln Asp Leu Leu Asp Arg Thr Arg Lys Pro Phe Gln Ser Val
            805                 810                 815

Ile Ala Asp Thr Gly Ile Ser Val Ser Glu Ile Asp His Val Val Leu
            820                 825                 830

Val Gly Gly Ser Thr Arg Met Pro Ala Val Thr Asp Leu Val Lys Glu
        835                 840                 845

Leu Thr Gly Gly Lys Glu Pro Asn Lys Gly Val Asn Pro Asp Glu Val
    850                 855                 860

Val Ala Val Gly Ala Ala Leu Gln Ala Gly Val Leu Lys Gly Glu Val
865                 870                 875                 880
```

```
Lys Asp Val Leu Leu Leu Asp Val Thr Pro Leu Ser Leu Gly Ile Glu
            885                 890                 895

Thr Lys Gly Gly Val Met Thr Arg Leu Ile Glu Arg Asn Thr Thr Ile
        900                 905                 910

Pro Thr Lys Arg Ser Glu Ser Phe Thr Thr Ala Asp Asp Asn Gln Pro
        915                 920                 925

Ser Val Gln Ile Gln Val Tyr Gln Gly Glu Arg Glu Ile Ala Ala His
        930                 935                 940

Asn Lys Leu Leu Gly Ser Phe Glu Leu Thr Gly Ile Pro Pro Ala Pro
945                 950                 955                 960

Arg Gly Ile Pro Gln Ile Glu Val Thr Phe Asp Ile Asp Ala Asn Gly
                965                 970                 975

Ile Val His Val Thr Ala Lys Asp Lys Gly Thr Gly Lys Glu Asn Thr
            980                 985                 990

Ile Arg Ile Gln Glu Gly Ser Gly  Leu Ser Lys Glu Asp  Ile Asp Arg
        995                 1000                1005

Met Ile Lys Asp Ala Glu Ala  His Ala Glu Glu Asp  Arg Lys Arg
    1010                1015                1020

Arg Glu Glu Ala Asp Val Arg  Asn Gln Ala Glu Thr  Leu Val Tyr
    1025                1030                1035

Gln Thr Glu Lys Phe Val Lys  Glu Gln Arg Glu Ala  Glu Gly Gly
    1040                1045                1050

Ser Lys Val Pro Glu Asp Thr  Leu Asn Lys Val Asp  Ala Ala Val
    1055                1060                1065

Ala Glu Ala Lys Ala Ala Leu  Gly Gly Ser Asp Ile  Ser Ala Ile
    1070                1075                1080

Lys Ser Ala Met Glu Lys Leu  Gly Gln Glu Ser Gln  Ala Leu Gly
    1085                1090                1095

Gln Ala Ile Tyr Glu Ala Ala  Gln Ala Ala Ser Gln  Ala Thr Gly
    1100                1105                1110

Ala Ala His Pro Gly Gly Glu  Pro Gly Gly Ala His  Pro Gly Ser
    1115                1120                1125

Ala Asp Asp Val Val Asp Ala  Glu Val Val Asp Asp  Gly Arg Glu
    1130                1135                1140

Ala Lys
    1145

<210> SEQ ID NO 3
<211> LENGTH: 3438
<212> TYPE: DNA
<213> ORGANISM: Artificial Sequence
<220> FEATURE:
<223> OTHER INFORMATION: HPV18&16/E6/E7HSP

<400> SEQUENCE: 3
atggccagat tcgaggaccc caccagacgg ccctacaagc tgcctgatct gtgcaccgag      60
ctgaacacca gcctgcagga catcgagatc acctgtgtgt actgcaagac cgtgctggaa     120
ctgaccgagg tgttcgagtt cgccttcaag gacctgttcg tggtgtaccg ggacagcatc     180
cctcacgccg cctgccacaa gtgcatcgac ttctacagcc ggatcagaga gctgcggcac     240
tacagcgaca gcgtgtacgg cgacaccctg gaaaagctga ccaacaccgg cctgtacaac     300
ctgctgatcc ggtgcctgag atgccagaag cccctgaatc ctgccggcgg actgagacac     360
ctgaacgaga agcggcggtt ccacaatatc gccggccact acagaggcca gtgccacagc     420
tgctgcaacc gggccagaca ggaacggctg cagcggagaa gagaaaccca gtgatgcac     480
```

```
ggccccaagg ccaccctgca ggatattgtg ctgcacctgg aaccccagaa cgagatcccc    540
gtggatctgc tgggacacgg ccagctgagc gactccgagg aagagaacga cgagatcgac    600
ggcgtgaacc accagcatct gcctgccaga agggccgagc ctcagagaca caccatgctg    660
tgcatgtgct gcaagtgcga ggcccggatc gagctggtgg tggaaagcag cgccgacgac    720
ctgagagcct tccagcagct gttcctgaac accctgagct tcgtgtgccc ttggtgcgcc    780
agccagcaga gcatgcacca gaaacggacc gccatgttcc aggaccccca ggaaagaccc    840
agaaagctgc cccagctgtg taccgaactg cagaccacca tccacgacat catcctggaa    900
tgcgtgtact gtaaacagca gctgctgagg cgcgaggtgt acgactttgc ctttcgggac    960
ctgtgcatcg tgtacaggga cggcaacccc tacgccgtgt gcgacaagtg cctgaagttc    1020
tacagcaaga tcagcgagta ccgccactac tgctactccc cgtacggcac cacactggaa    1080
cagcagtaca acaagcccct gtcgcatctg ctgatcagat gcatcaactg ccagaaacct    1140
ctgtgccccg agggcggcca gaggcacctg ataagaagc agagattcca caacatccgg    1200
ggcagatgga ccggcagatg catgtcctgc tgcagaagca gccggaccag acgggaaaca    1260
cagctgatgc atggcgatac ccctaccctg cacgagtaca tgctggacct gcagcccgag    1320
acaaccgatc tgtacggcta cggacagctg aacgacagct ctgaagaaga ggacgaaatt    1380
gacggccctg ccggccaggc cgaacctgat agagcccact acaatatcgt gaccttctgt    1440
tgcaagtgtg acagcaccct gcggctgtgc gtgcagagca cacgtggaa catccggacc    1500 ctggaagatc tgctgatggg caccctgggc atcgtgtgtc ccatctgcag ccagaaaccc    1560
atggccagag ccgtgggcat cgatctgggc accaccaaca gcgtggtgtc tgtgctggaa    1620
gggggcgacc ctgtggtggt ggccaatagc gagggcagca gaaccacccc tagcatcgtg    1680
gccttcgccc ggaatggcga agtgctcgtg ggacagcccg ccaagaatca ggccgtgacc    1740
aacgtggaca gaaccgtgcg gagcgtgaag cggcacatgg gcagcgattg gagcatcgag    1800
attgacggca agaagtacac cgcccctgag atcagcgccc ggatcctgat gaagctgaag    1860
agggacgccg aggcctacct gggcgaggat atcaccgatg ccgtgatcac cacccccgcc    1920
tacttcaacg acgcccagag acaggccacc aaggacgccg acagatcgc cggactgaac    1980 gtgctgcgga tcgtgaacga gcctacagcc gccgctctgg cctacggact ggacaagggc    2040
gagaaagaac agcggatcct ggtgttcgac ctgggcggag gcaccttcga tgtgtccctg    2100
ctggaaatcg cgagggcgt ggtggaagtg cgggccacat ctggcgataa ccacctggga    2160
ggcgacgact gggaccagag agtggtggac tggctggtgg acaagttcaa gggcaccagc    2220
ggcatcgacc tgaccaagga caagatggcc atgcagcggc tgagagaggc cgccgagaag    2280
gccaagattg agctgagcag cagccagagc acctccatca acctgcccta catcaccgtg    2340
gacgccgaca gaacccccct gttcctggac gagcagctga ccagagccga gttccagcgg    2400
atcacccagg acctgctgga caggaccaga aagcccttcc agagcgtgat cgccgacacc    2460
ggcatcagcg tgtccgagat cgatcacgtg gtgctcgtgg gcggcagcac cagaatgcct    2520
gccgtgaccg acctcgtgaa agagctgacc ggcggcaaag aacccaacaa gggcgtgaac    2580
cccgacgagg tggtggctgt gggagctgca ctgcaggcag gcgtgctgaa gggcgaagtg    2640
aaggacgtgc tgctgctgga cgtgacccct ctgagcctgg aatcgagac aaagggcgga    2700 gtgatgaccc ggctgatcga gagaaacacc acaatcccca ccaagcggag cgagagcttc    2760
accaccgccg acgataacca gcccagcgtg cagatccagg tgtaccaggg cgagagagag    2820
```

-continued

```
atcgccgccc acaacaagct gctgggcagc ttcgagctga caggcatccc accagccccc    2880
agaggaatcc ctcagatcga agtgaccttc gacatcgacg ccaacggcat cgtgcacgtg    2940
accgccaagg ataagggcac cggcaaagag aacaccatcc ggatccagga aggcagcggc    3000
ctgagcaaag aggatatcga cagaatgatc aaggatgccg aggcccacgc cgaagaggac    3060
cggaaaagac gggaagaggc cgacgtgcgg aaccaggctg agacactggt gtatcagacc    3120
gagaagtttg tgaaagagca gcgcgaggcc gagggcggat ctaaggtgcc agaggacacc    3180
ctgaacaagg tggacgctgc cgtggccgaa gccaaggctg ctctgggagg cagcgatatc    3240
agcgccatca agagcgccat ggaaaaactg ggccaggaaa gccaggccct ggggcaggcc    3300
atctatgaag ctgctcaggc tgccagccag gctacaggcg ctgctcatcc tggcggagaa    3360
ccaggcggag cccatccagg atctgccgat gacgtggtgg atgccgaagt ggtggacgac    3420
ggccgggaag ccaaatga                                                  3438
```

```
<210> SEQ ID NO 4
<211> LENGTH: 435
<212> TYPE: DNA
<213> ORGANISM: Artificial Sequence
<220> FEATURE:
<223> OTHER INFORMATION: GM-CSF

<400> SEQUENCE: 4
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagat tatcaccttt    360
gaaagtttca aagagaacct gaaggacttt ctgcttgtca tcccctttga ctgctgggag    420
ccagtccagg agtga                                                    435
```